United States Patent
Gross et al.

(10) Patent No.: US 8,585,720 B2
(45) Date of Patent: *Nov. 19, 2013

(54) SUTURE TRIMMER

(75) Inventors: T. Daniel Gross, Los Gatos, CA (US); Maurice Marthaler, Santa Rosa, CA (US); Michael Scott Dana, Newark, CA (US); Dawn Ma, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/539,095

(22) Filed: Jun. 29, 2012

(65) Prior Publication Data

US 2013/0030451 A1  Jan. 31, 2013

Related U.S. Application Data

(63) Continuation of application No. 10/027,681, filed on Dec. 21, 2001, now Pat. No. 8,211,123.

(51) Int. Cl.
*A61B 17/04* (2006.01)

(52) U.S. Cl.
USPC .......................... 606/148; 606/138; 606/167

(58) Field of Classification Search
USPC .......... 606/148, 138, 167, 170–171; 112/689; 604/22; 30/135, 234, 261
See application file for complete search history.

(56) References Cited

U.S. PATENT DOCUMENTS

| | | |
|---|---|---|
| 3,328,876 A | 7/1967 | Hoppe |
| 3,372,477 A | 3/1968 | Hoppe |
| 3,380,448 A | 4/1968 | Sadove et al. |
| 3,625,556 A | 12/1971 | Stromberg |
| 3,752,516 A | 8/1973 | Mumma |
| 3,840,017 A | 10/1974 | Violante |
| 4,246,698 A | 1/1981 | Lasner et al. |
| 4,369,787 A | 1/1983 | Lasner et al. |
| 4,527,331 A | 7/1985 | Lasner et al. |
| 4,602,635 A | 7/1986 | Mulhollan et al. |
| 4,641,652 A | 2/1987 | Hutterer et al. |

(Continued)

FOREIGN PATENT DOCUMENTS

| | | |
|---|---|---|
| DE | 9112301 | 1/1992 |
| DE | 9214580 | 4/1994 |

(Continued)

OTHER PUBLICATIONS

U.S. Appl. No. 10/004,817, Dec. 18, 2002, Office Action.

(Continued)

*Primary Examiner* — Gary Jackson
*Assistant Examiner* — Diane Yabut
(74) *Attorney, Agent, or Firm* — Workman Nydegger; Randy Shen

(57) ABSTRACT

In accordance with the present invention there is provided a suture trimmer, the suture trimmer comprising a shaft having a proximal end and a distal end and an axis therebetween, the shaft having a groove formed in the side thereof, the groove in communication with an opening formed in the side of the shaft, the opening disposed proximal the distal end. The suture trimmer further including a cutting member slidably disposed within the shaft, and a suture retainer slidably disposed within the shaft. Wherein the suture trimmer in accordance with the present invention may be additionally utilized to position knots formed within a suture loop prior to trimming the free end(s) of the suture loop.

20 Claims, 11 Drawing Sheets

(56) References Cited

U.S. PATENT DOCUMENTS

| | | |
|---|---|---|
| 4,957,498 A | 9/1990 | Caspari et al. |
| 4,961,741 A | 10/1990 | Hayhurst |
| 5,059,201 A * | 10/1991 | Asnis ............... 606/144 |
| 5,133,723 A | 7/1992 | Li et al. |
| 5,176,691 A | 1/1993 | Pierce |
| 5,176,695 A | 1/1993 | Dulebohn |
| 5,242,459 A * | 9/1993 | Buelna ............... 606/148 |
| 5,269,791 A | 12/1993 | Mayzels et al. |
| 5,292,327 A | 3/1994 | Dodd et al. |
| 5,304,190 A | 4/1994 | Reckelhoff et al. |
| 5,312,423 A | 5/1994 | Rosenbluth et al. |
| 5,342,459 A | 8/1994 | Klemp et al. |
| 5,403,330 A | 4/1995 | Tuason |
| 5,405,351 A | 4/1995 | Kinet et al. |
| 5,405,354 A | 4/1995 | Sarrett |
| 5,417,699 A | 5/1995 | Klein et al. |
| 5,423,837 A | 6/1995 | Mericle et al. |
| 5,462,562 A | 10/1995 | Elkus |
| 5,520,702 A | 5/1996 | Sauer et al. |
| 5,527,322 A | 6/1996 | Klein et al. |
| 5,549,617 A | 8/1996 | Green et al. |
| 5,549,618 A | 8/1996 | Fleenor et al. |
| 5,565,122 A | 10/1996 | Zinnbauer et al. |
| 5,585,122 A | 12/1996 | Drum et al. |
| 5,643,289 A | 7/1997 | Sauer et al. |
| 5,649,939 A | 7/1997 | Reddick |
| 5,669,917 A | 9/1997 | Sauer et al. |
| 5,704,943 A | 1/1998 | Yoon et al. |
| 5,746,752 A | 5/1998 | Burkhart |
| 5,797,928 A | 8/1998 | Kogasaka |
| 5,797,929 A * | 8/1998 | Andreas et al. ............... 606/148 |
| 5,830,234 A | 11/1998 | Wojciechowicz et al. |
| 5,860,993 A | 1/1999 | Thompson et al. |
| 5,879,371 A | 3/1999 | Gardiner et al. |
| 5,997,555 A | 12/1999 | Kontos |
| 6,004,295 A | 12/1999 | Langer et al. |
| 6,007,544 A | 12/1999 | Kim |
| 6,045,570 A | 4/2000 | Epstein et al. |
| 6,051,004 A | 4/2000 | Gill |
| 6,077,277 A | 6/2000 | Mollenauer et al. |
| 6,077,279 A | 6/2000 | Kontos |
| 6,090,063 A * | 7/2000 | Makower et al. ............... 604/13 |
| 6,132,439 A | 10/2000 | Kontos |
| 6,171,317 B1 | 1/2001 | Jackson et al. |
| 6,254,620 B1 | 7/2001 | Koh et al. |
| 6,261,272 B1 | 7/2001 | Gross et al. |
| 6,527,785 B2 | 3/2003 | Sancoff et al. |
| 6,620,185 B1 | 9/2003 | Harvie et al. |
| 6,733,509 B2 | 5/2004 | Nobles et al. |
| 6,746,457 B2 | 6/2004 | Dana et al. |
| 6,860,890 B2 | 3/2005 | Bachman et al. |
| 7,094,246 B2 | 8/2006 | Anderson et al. |
| 7,147,646 B2 | 12/2006 | Dana et al. |
| 7,842,051 B2 | 11/2010 | Dana et al. |
| 7,918,867 B2 | 4/2011 | Dana et al. |
| 7,992,571 B2 | 8/2011 | Gross et al. |
| 8,211,123 B2 * | 7/2012 | Gross et al. ............... 606/148 |
| 2011/0106104 A1 | 5/2011 | Dana et al. |

FOREIGN PATENT DOCUMENTS

| | | |
|---|---|---|
| EP | 0669103 | 9/1999 |
| WO | WO 94/08515 | 4/1994 |
| WO | WO 95/32669 | 12/1995 |
| WO | WO 00/69342 | 11/2000 |
| WO | WO 02/15795 | 2/2002 |
| WO | WO 03/049621 | 6/2003 |
| WO | WO 03/059174 | 7/2003 |

OTHER PUBLICATIONS

U.S. Appl. No. 10/004,817, Jul. 28, 2003, Notice of Allowance.
U.S. Appl. No. 10/004,817, Feb. 4, 2004, Notice of Allowance.
U.S. Appl. No. 10/027,681, Jun. 2, 2003, Office Action.
U.S. Appl. No. 10/027,681, Dec. 8, 2003, Office Action.
U.S. Appl. No. 10/027,681, May 28, 2004, Office Action.
U.S. Appl. No. 10/027,681, Oct. 23, 2006, Office Action.
U.S. Appl. No. 10/027,681, Apr. 17, 2007, Office Action.
U.S. Appl. No. 10/027,681, Oct. 30, 2007, Office Action.
U.S. Appl. No. 10/027,681, May 27, 2008, Office Action.
U.S. Appl. No. 10/027,681, Dec. 23, 2008, Office Action.
U.S. Appl. No. 10/027,681, Jul. 8, 2009, Office Action.
U.S. Appl. No. 10/027,681, Feb. 17, 2010, Office Action.
U.S. Appl. No. 10/027,681, Aug. 16, 2010, Office Action.
U.S. Appl. No. 10/027,681, Jan. 19, 2011, Office Action.
U.S. Appl. No. 10/027,681, Feb. 3, 2012, Office Action.
U.S. Appl. No. 10/027,681, Apr. 5, 2012, Notice of Allowance.
U.S. Appl. No. 10/324,730, Mar. 27, 2006, Office Action.
U.S. Appl. No. 10/324,730, Aug. 8, 2006, Office Action.
U.S. Appl. No. 10/324,730, Jan. 29, 2007, Office Action.
U.S. Appl. No. 10/324,730, Aug. 30, 2007, Notice of Allowance.
U.S. Appl. No. 10/324,730, Aug. 19, 2008, Office Action.
U.S. Appl. No. 10/324,730, Oct. 30, 2009, Notice of Allowance.
U.S. Appl. No. 10/324,730, Mar. 23, 2010, Notice of Allowance.
U.S. Appl. No. 10/324,730, Sep. 22, 2010, Notice of Allowance.
U.S. Appl. No. 10/661,155, Aug. 31, 2005, Office Action.
U.S. Appl. No. 10/661,155, Feb. 23, 2006, Notice of Allowance.
U.S. Appl. No. 10/860,443, May 17, 2006, Office Action.
U.S. Appl. No. 10/860,443, Oct. 2, 2006, Notice of Allowance.
U.S. Appl. No. 11/461,243, Apr. 29, 2009, Office Action.
U.S. Appl. No. 11/461,243, Oct. 21, 2009, Office Action.
U.S. Appl. No. 11/461,243, Mar. 15, 2010, Office Action.
U.S. Appl. No. 11/461,243, Jul. 28, 2010, Notice of Allowance.
U.S. Appl. No. 11/461,243, Nov. 10, 2010, Issue Notification.
U.S. Appl. No. 11/465,035, Nov. 28, 2008, Office Action.
U.S. Appl. No. 11/465,035, Mar. 4, 2010, Office Action.
U.S. Appl. No. 11/465,035, Jun. 22, 2010, Office Action.
U.S. Appl. No. 11/465,035, Mar. 31, 2011, Notice of Allowance.
U.S. Appl. No. 12/914,658, Nov. 19, 2012, Office Action.
U.S. Appl. No. 12/914,658, Mar. 7, 2013, Notice of Allowance.
U.S. Appl. No. 12/914,658, Jun. 19, 2013, Issue Notification.

* cited by examiner

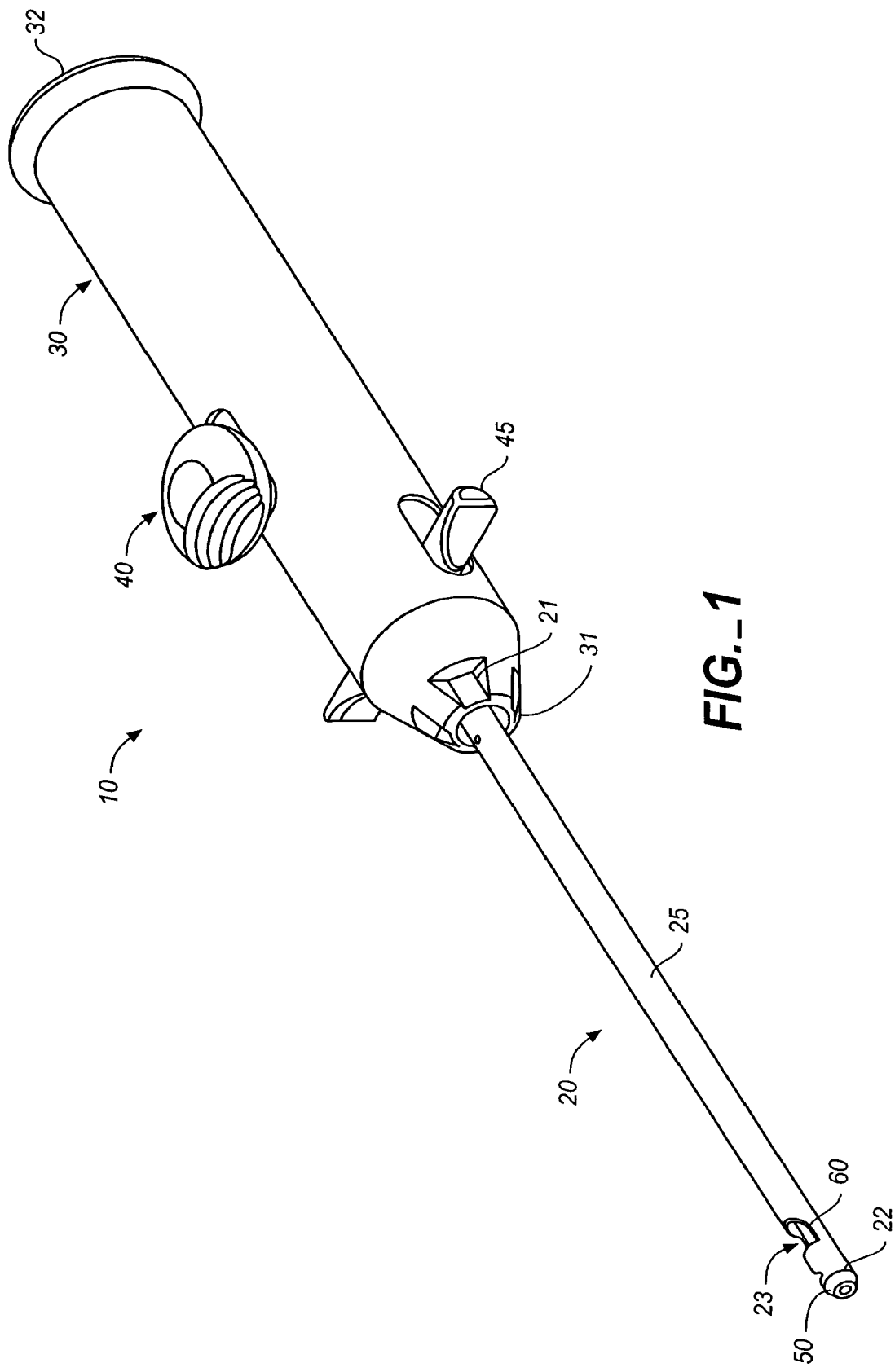

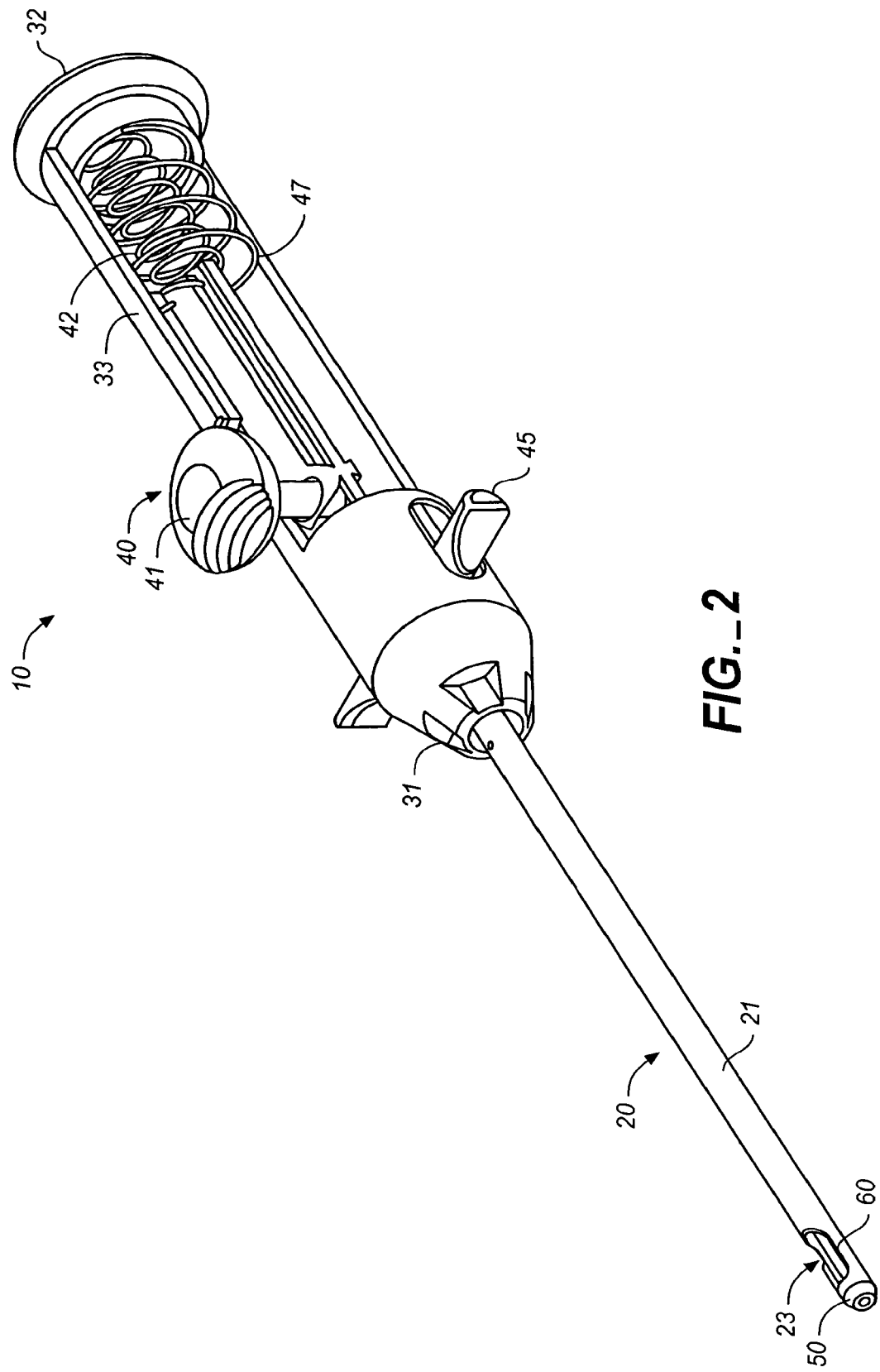
FIG._2

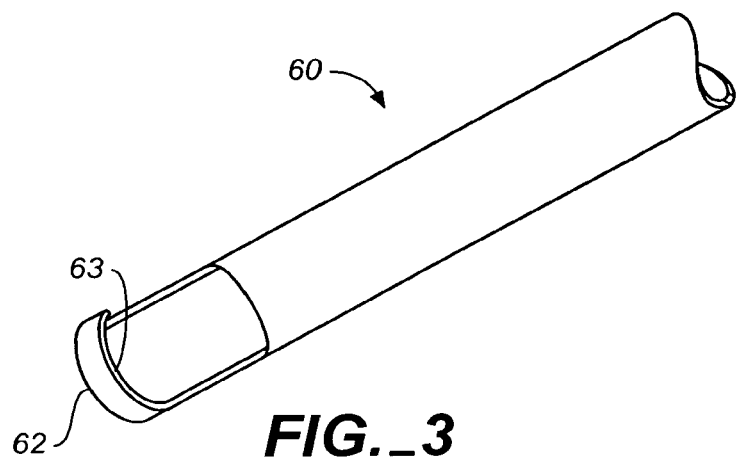
FIG._3
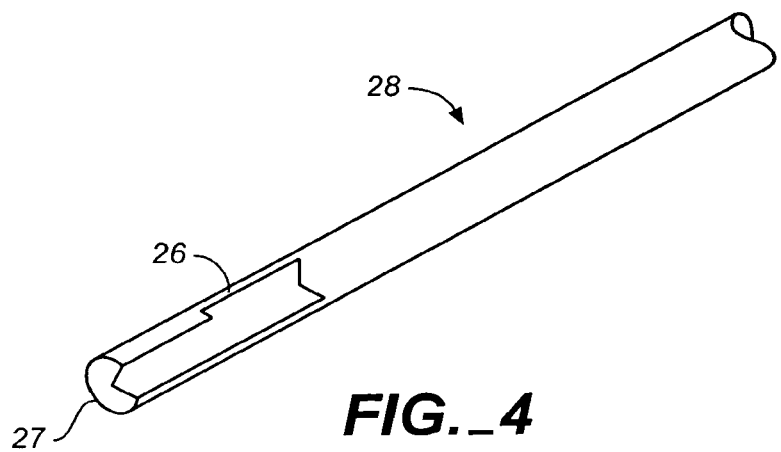
FIG._4

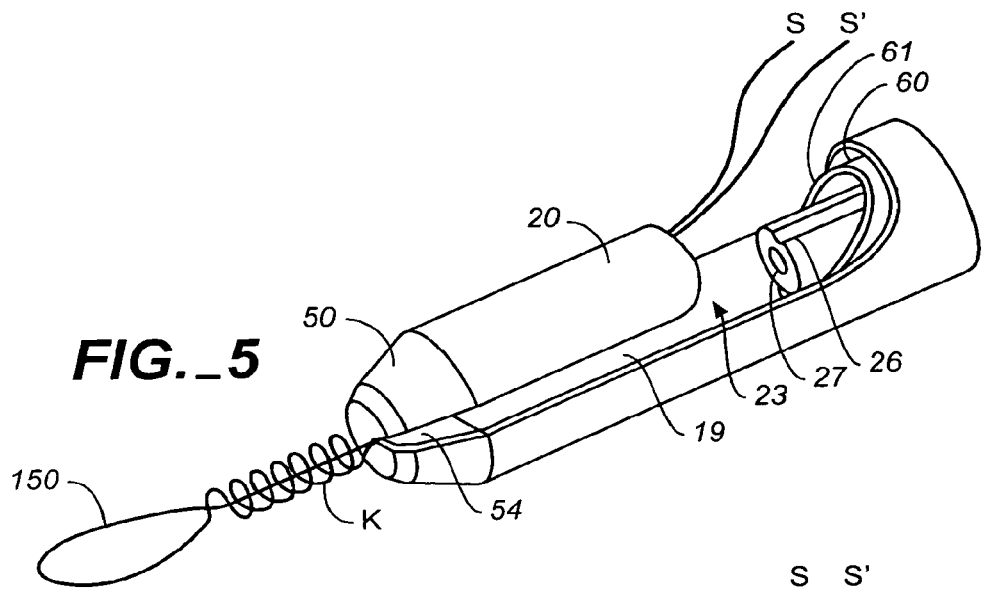
FIG._5
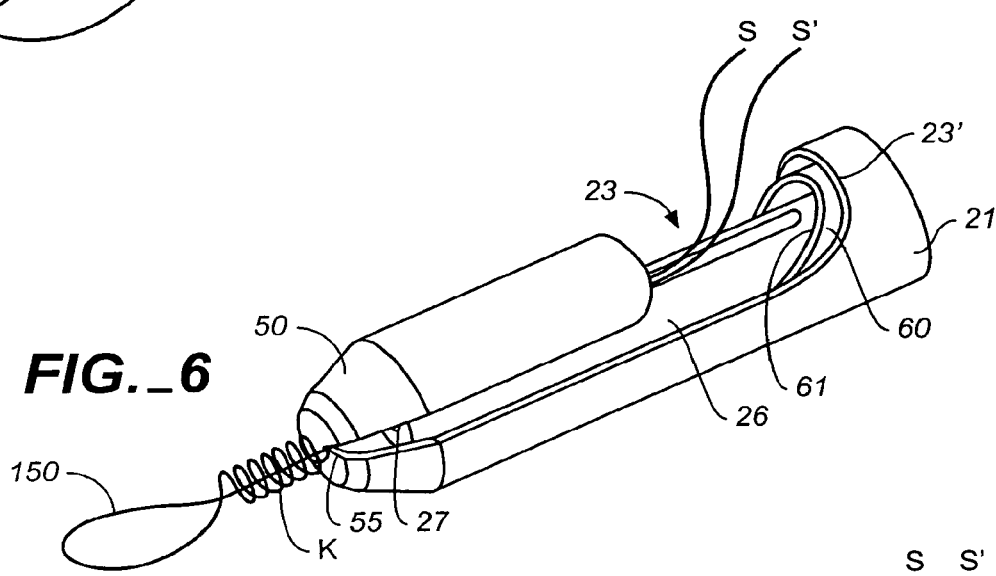
FIG._6
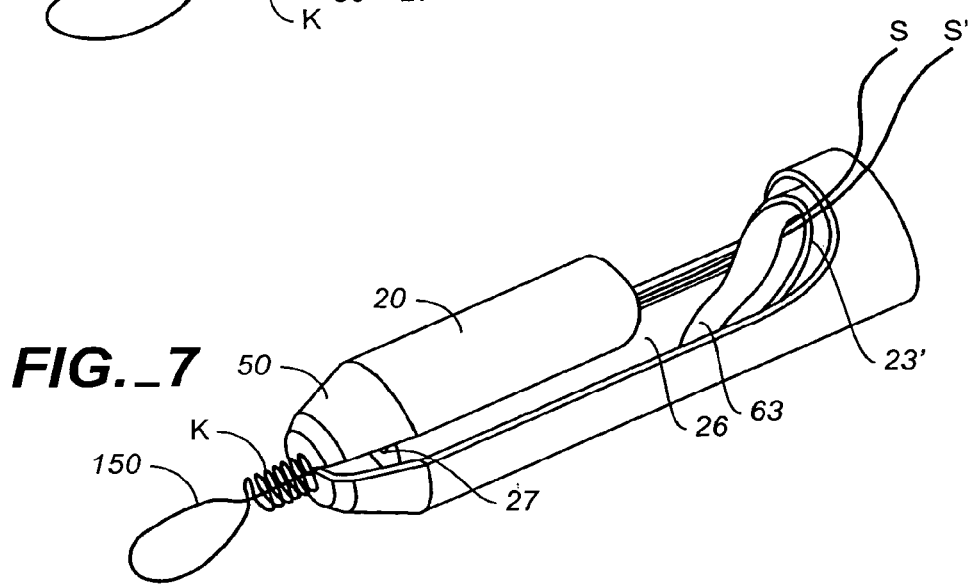
FIG._7

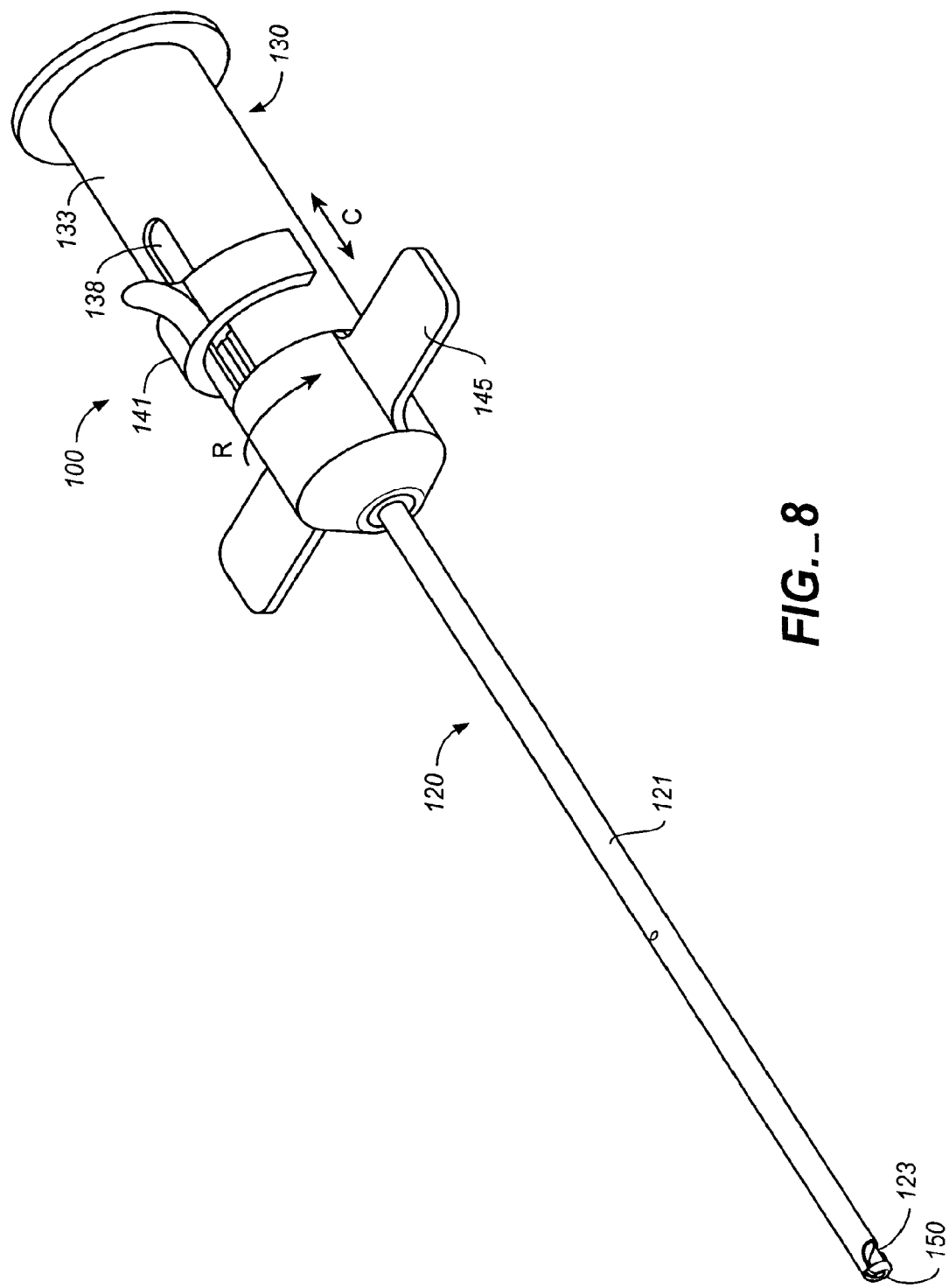
FIG._8

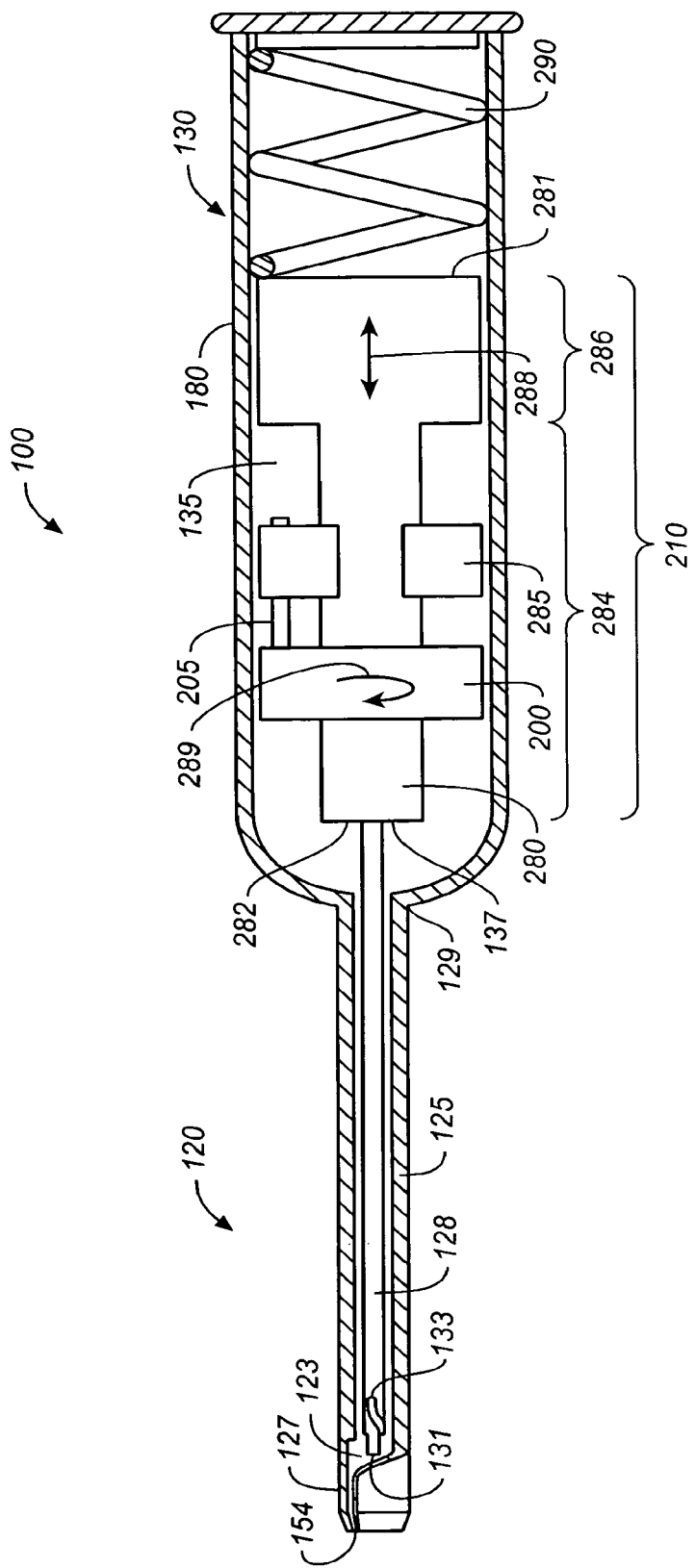
FIG._9

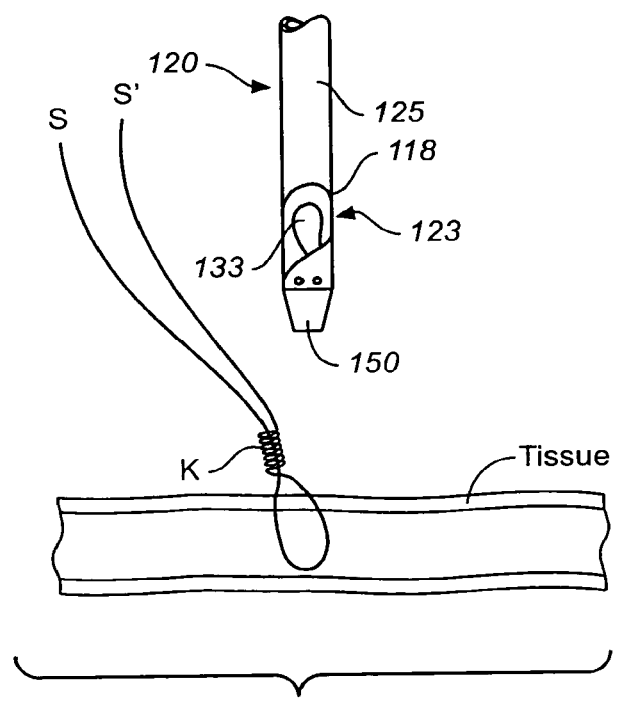
FIG._10
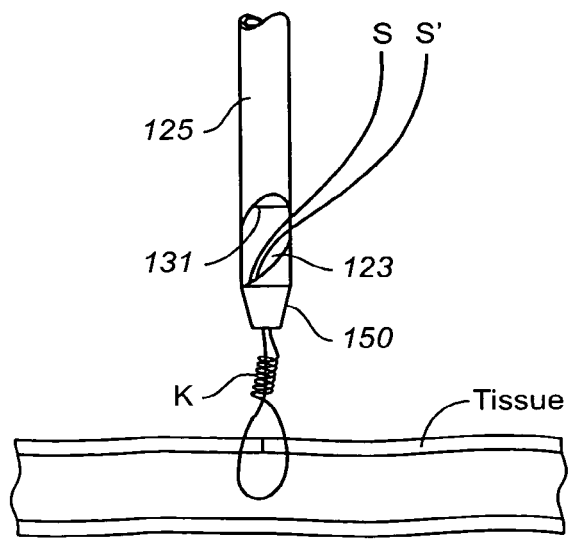
FIG._11

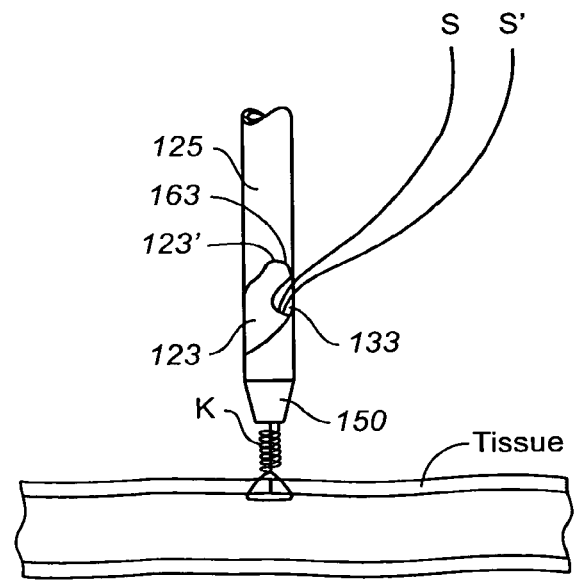
FIG._12
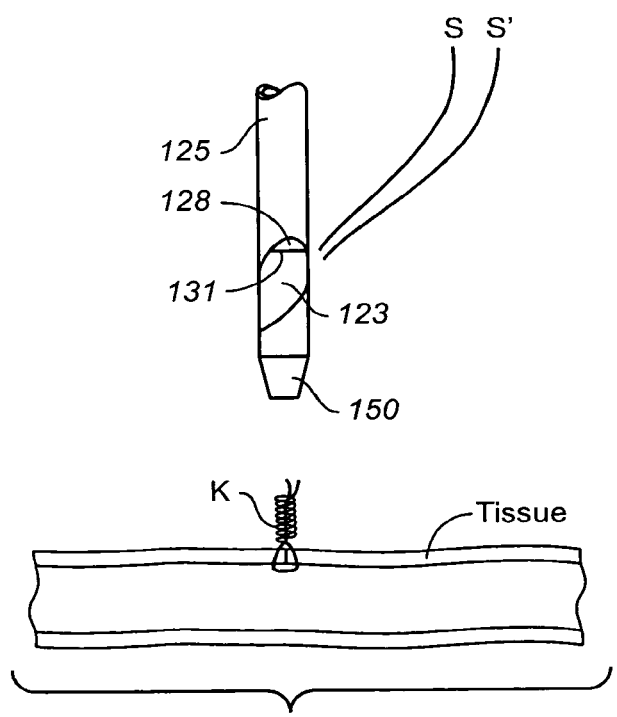
FIG._13

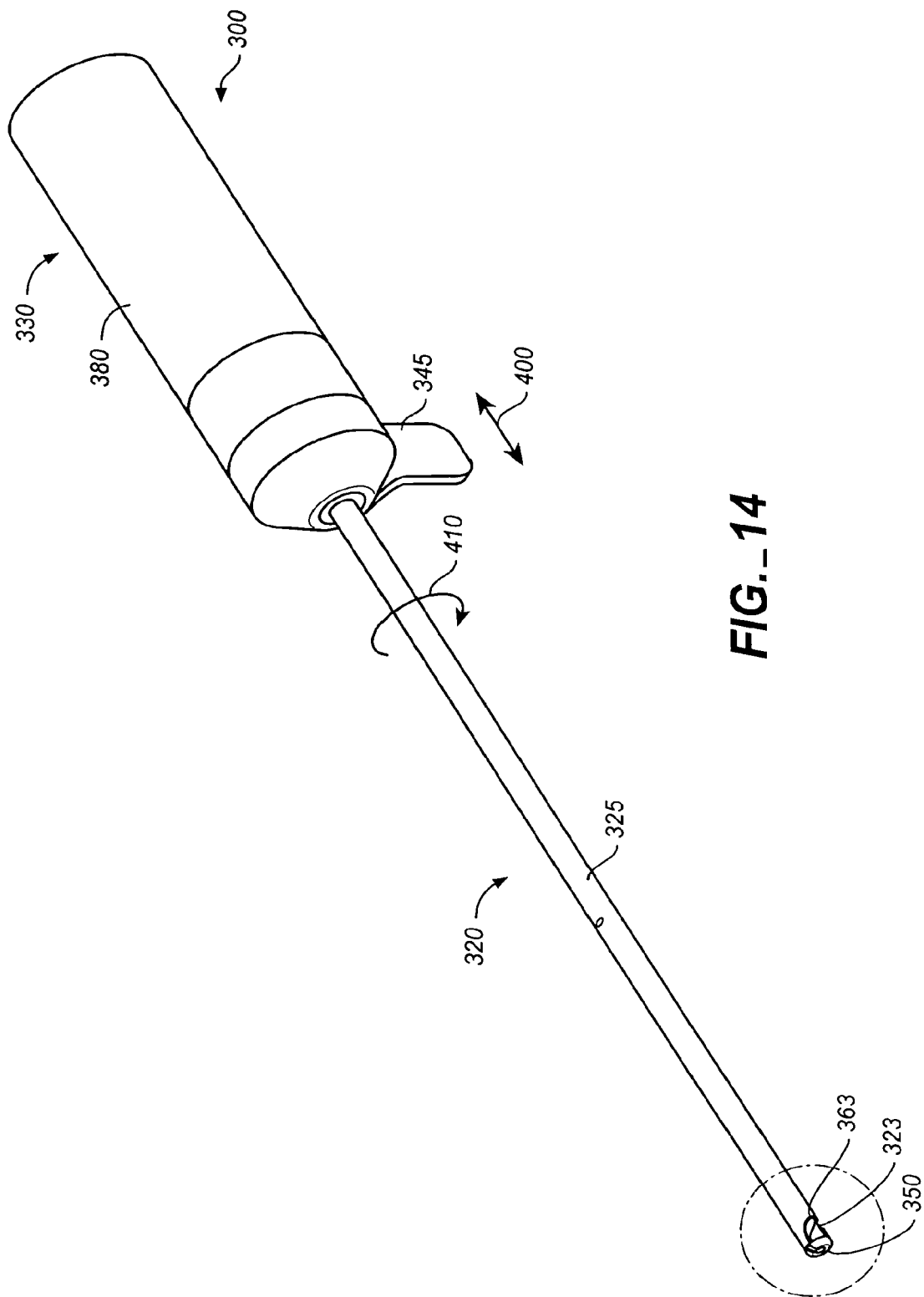
FIG._14

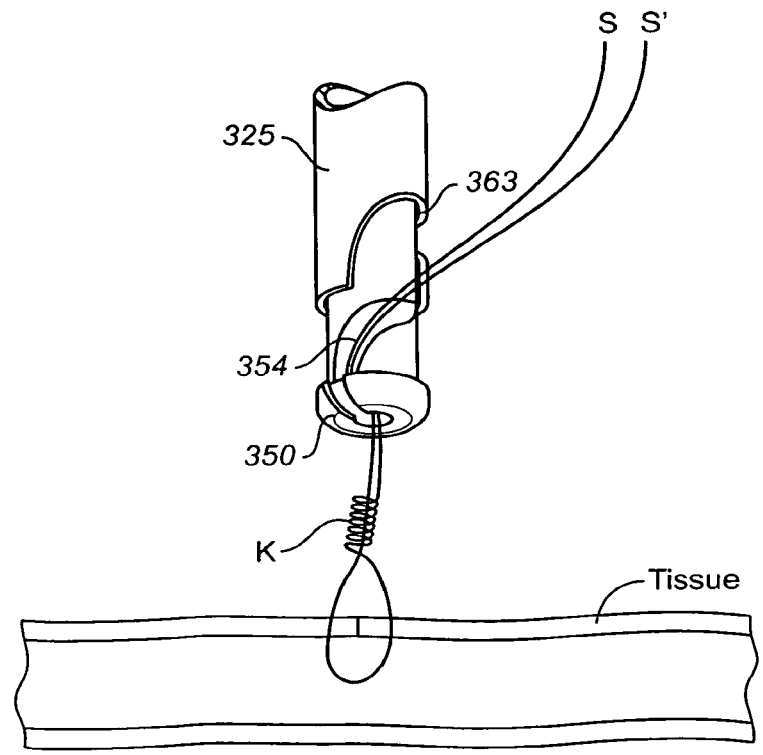
FIG._15
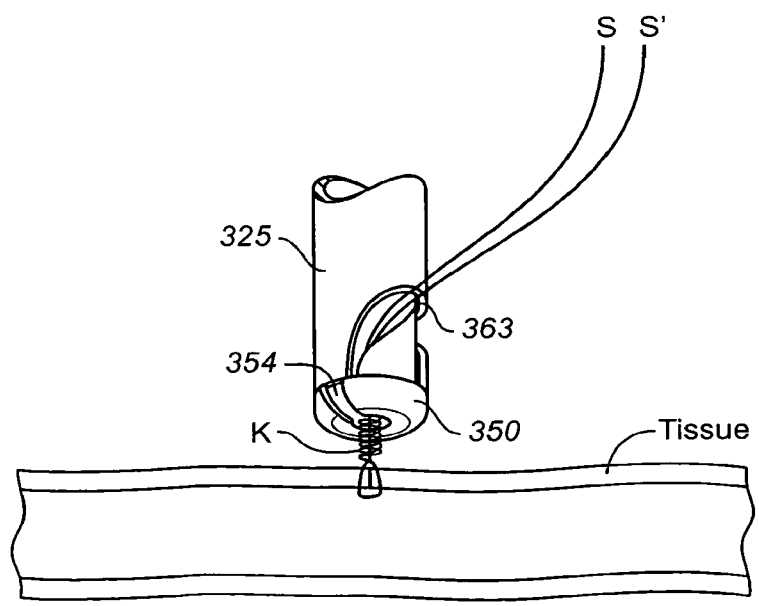
FIG._16

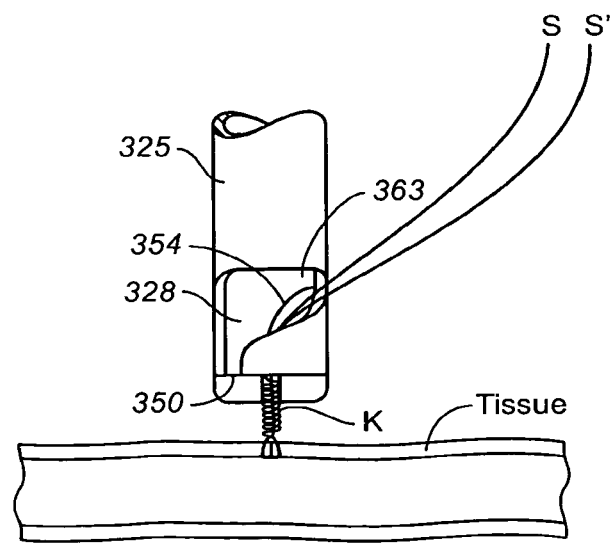
FIG._17
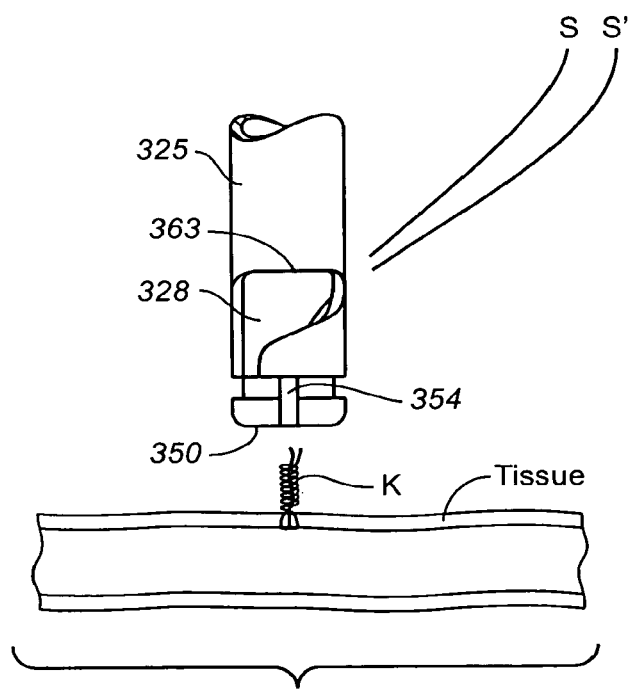
FIG._18

SUTURE TRIMMER

CROSS-REFERENCE TO RELATED APPLICATIONS

The present application is a Continuation of U.S. patent application Ser. No. 10/027,681, entitled "SUTURE TRIMMER" filed on Dec. 21, 2001, issued as U.S. Pat. No. 8,211,123 on Jul. 3, 2012. The preceding application is hereby incorporated by reference in its entirety.

FIELD OF THE INVENTION

The present-invention relates generally to surgical devices and methods. More particularly, the present invention relates to the construction and use of devices for advancing surgical knot(s) and trimming the ends of the suture adjacent to the knot(s). Such a device is to be referred to as a "suture trimmer", as used through the appended specification.

BACKGROUND OF THE INVENTION

The closing of incisions and wounds using suture is a preferred technique of surgeons and many other physicians. While other techniques are now available such as stapling, the use of "tissue glues," and the use of collagen for closing vascular punctures, the use of suture is often preferred because it provides a reliable and tight closure of any wound. Additionally, if a suture is to fail, the surgeon will know immediately. In contrast, many of the other devices listed above which may not fail until some time after the procedure.

While the suturing of a wound is a relatively straightforward procedure in most open surgical procedures, placement and tying of sutures in laprascopic and other minimally invasive procedures can be problematic. In order to provide for suturing under such circumstances, a variety of devices have been developed for the remote placement and tying of suture through cannulas under video observation. Usually, a sliding knot will be formed in a suture loop, a tool known as a "knot pusher" such as that shown in U.S. Pat. No. 5,797,929 the entirety of which is hereby incorporated by reference, is utilized to advance and position the knot and tighten the loop of suture.

Such knot pushing devices may also be utilized in recently developed techniques for the remote suturing of vascular punctures. Punctures may be formed in the femoral or other arteries to provide vascular access for performing angioplasty and other vascular procedures. Such techniques are described in U.S. Pat. No. 5,417,699 and U.S. Pat. No. 5,527,322 the entirety of which are hereby incorporated by reference. Such methods result in the placement of a suture loop through tissue on opposite sides of the vascular puncture. Two free ends of the suture loop are brought out through a tissue tract leading to the puncture, and the ends may be externally tied by the treating physician. Alternatively, a knot forming device such as that shown in U.S. Pat. No. 6,171,317, the entirety of which is hereby incorporated by reference, may be utilized to tie a knot.

Through the use of a knot pusher, such as that shown and described in U.S. Pat. No. 5,797,929 the knot may be advanced through the tissue tract so that it lies directly over the adventitial wall of the blood vessel.

After the knot has been advanced over the adventitial wall of the blood vessel and tightened, the excess suture must be cut away. Typically, a surgeon may utilize a scalpel or a pair of scissors to cut the suture ends just below the exterior surface of the patient's skin.

A concern with this method is that by leaving lengths of suture within the wound may lead to irritation of the incision. More significantly, a relatively long suture end, extending from the knot at the vessel repair to the-skin level, may act as a "wick" for infective microorganisms which may be present at skin level. The wick would provide a conduit for these microorganisms to travel from the skin surface to the vessel repair, thereby leading to infection. Many times a surgeon cannot easily shorten this cut length because the location of the knot is well below the patient's tissue and is not readily visible, therefore they can only shorten the suture to the point that they can visually see.

Further still, many surgical procedures are moving away from being open and toward being minimally invasive wherein the procedure is performed within a small opening formed in the patient's tissue. As described above, many times the surgeon cannot see the vessel which they are trying to close with the suture.

Therefore there is a need for a device that will enable a surgeon to advance a knot and trim the excess suture from the knot without having to visually see the knot.

SUMMARY OF THE INVENTION

In accordance with the present invention there is provided a suture trimmer, the suture trimmer including a shaft having a proximal end and a distal end and an axis therebetween, the shaft having a slot formed in the side thereof, the slot in communication with an opening formed in the side of the shaft, the opening disposed proximal the distal end. The suture trimmer further including a cutting member slidably disposed within the shaft, and a suture retainer slidably disposed within the shaft.

In accordance with another aspect in accordance with the present invention there is provided a method for trimming suture, the method including the steps of disposing a suture loop within tissue of a patient, the suture loop including at least one knot and at least one free end of suture. The method further including the step of disposing the free end of suture through a groove and opening formed in a distal end of a suture trimmer, wherein a cutting member is actuated within the suture trimmer, the cutting member configured to sever the suture disposed in the opening.

DETAILED DESCRIPTION OF THE DRAWINGS

The objects and advantages of the invention will become apparent from the following detailed description of preferred embodiments thereof in connection with the accompanying drawings in which like numerals designate like elements and in which:

FIG. 1 is a isometric view of an exemplary embodiment of a suture trimmer in accordance with the present invention;

FIG. 2 is a partial cut-away isometric view of the suture trimmer in accordance with the present invention;

FIG. 3 is a partial perspective view of the cutting member in accordance with the present invention;

FIG. 4 is a partial perspective view of the suture retainer in accordance with the present invention;

FIG. 5 is a partial isometric view of the distal tip of the suture trimmer in accordance with the present invention illustrating a suture loop disposed therethrough and the suture retainer is in a retracted position;

FIG. 6 is a partial isometric view of the distal tip of the suture trimmer in accordance with the present invention illustrating a suture loop being disposed therethrough wherein the suture retainer is in a deployed position;

FIG. 7 is a partial isometric view of the distal tip of the suture trimmer in accordance with the present invention illustrating a suture loop being disposed therethrough wherein the cutting member has been activated;

FIG. 8 is an isometric view of an alternative embodiment of a suture trimmer in accordance with the present invention;

FIG. 9 is a cross-sectional view of the suture trimmer in accordance with FIG. 8 illustrating the slider assembly disposed within the handle;

FIG. 10 is a partial view of the distal tip of the suture trimmer in accordance with FIG. 8, wherein a suture loop has been formed in a patient's tissue;

FIG. 11 is a partial view of the distal tip of the suture trimmer of FIG. 8, wherein the suture retainer has been retracted;

FIG. 12 is a partial view of the distal tip of the suture trimmer of FIG. 8, wherein the suture retainer has been rotated to align the free ends of the suture with the cutting edge formed in the opening of the shaft of the suture trimmer;

FIG. 13 is a partial view of the distal tip of the suture trimmer of FIG. 8, wherein the suture retainer has been retracted;

FIG. 14 is perspective view of yet another alternative embodiment of a suture trimmer in accordance with the present invention;

FIG. 15 is a sectional view of the distal tip of the suture trimmer in accordance with FIG. 14 illustrating the elongated member in a retracted position;

FIG. 16 is a sectional view of the distal tip of the suture trimmer in accordance with FIG. 14, wherein the suture retainer has been retraced to retain at least one suture in the distal tip;

FIG. 17 is a sectional view of the distal tip of the suture trimmer in accordance with FIG. 14, wherein an outer sheath of the suture trimmer has been rotated to a cutting position; and FIG. 18 is a sectional view of the distal tip of the suture trimmer in accordance with FIG. 14, wherein the outer sheath has been retracted to trim the suture.

DETAILED DESCRIPTION OF A PREFERRED EMBODIMENT

In accordance with the present invention there is provided a suture trimmer, the suture trimmer may be utilized by physicians in any of a variety of surgical procedures where suture loop has been formed in tissue to close an incision or wound, or for any other purpose. A slidable knot will be formed in the suture loop, and the suture trimmer is used to engage and advance the knot over a free end of the suture to close the suture loop. The knot can then be tightened by pulling on the other free end of the suture. The free ends of the suture may then be trimmed adjacent to the knot by actuating the cutting member of the suture trimmer.

Referring now to FIG. 1 there is shown an exemplary embodiment of a suture trimmer in accordance with the present invention. The suture trimmer comprises a shaft assembly having a proximal end and distal end, a handle disposed at the proximal end of the shaft, a first and second lever extending from the handle, wherein the first lever and second lever are operatively associated with a cutting member and a suture retaining device respectively.

As shown in FIG. 1, the suture trimmer includes a shaft assembly 20. The shaft assembly 20 includes an elongated member 25 having a proximal end 21 and a distal end 22. An opening 23 is formed in the elongated member 25 adjacent to the distal end 22. A fitting 50 may be disposed adjacent to the distal end 22 of the shaft assembly 20. The fitting 50 having a cross-sectional size no greater than that of the elongated member 25. The fitting 50 further including a groove formed therein, wherein the groove is adapted to receive at least one length of suture therethrough. In a preferred embodiment, the groove is configured to receive at least two sutures therethrough. The distal face of the fitting 50 is configured to engage a knot formed in a suture loop, thereby enabling the suture trimmer 10 to be utilized as a knot pusher and advance the knot to an incision site. The face of the fitting may be formed having a convex, concave, or flat surface. Alternatively, the face may be formed at an angle relative to an axis extending through the shaft assembly.

The fitting may be retained within the bore of the elongated member through the use of mechanical fasteners or suitable adhesives. It is further contemplated that the fitting may be formed onto the elongated member utilizing a molding process. Alternatively, the fitting and elongated member may be integrally formed. The fitting is preferably fabricated of a bio-compatible material, such as metal or plastic.

The shaft assembly 20 further comprises a cutting member 60 and a suture retaining member 28 disposed within the bore of the elongated member. The cutting member 60 and the suture retaining member 28 may be retained within the bore of the elongated member coaxially, though it is contemplated that they may be retained in other manners, such as, side-by-side or offset. Both the cutting member 60 and the suture retaining member 28 are slidably disposed within the bore of the elongated member.

As shown in FIG. 3 the cutting member 60 comprises an elongated member having a proximal end and a distal end 62. An cutting edge 63 is formed within the cutting member 60 adjacent to the distal end 62. A lever 45 is coupled to the cutting member 60 adjacent to the proximal end. The lever 45 is further configured to engage a biasing member 42 as shown in FIG. 2.

The cutting member 60 may be constructed of a bio-compatible material, such that the material chosen is capable of having a sufficiently sharp cutting edge 63 formed therein. For example, surgical stainless steel may be utilized as well as titanium. Furthermore, it is contemplated that the cutting member may comprise one or more elements coupled together. For example the shaft of the cutting member may be constructed of a bio-compatible material such as plastic and the cutting edge 63 may be formed of metal wherein the two pieces are combined to form a single element.

Referring now to FIG. 4, there is shown the suture retainer in accordance with the present invention. As shown in FIG. 4, the suture retainer 28 includes a proximal end, a distal end 27, and a suture protector 26. The suture protector 26 disposed adjacent the distal end 27 of the suture retainer 28. A lever 41 is connected to the proximal end 29 of the suture retainer 28. The lever is configured to be slidably received within the handle 33 as shown in FIG. 2. The lever 41 is further configured to receive a biasing member 47, wherein the biasing member retains the suture retainer in a position wherein the suture retainer projects into the opening 23 formed in the elongated member of the shaft assembly 20.

The suture retainer may be constructed of a bio-compatible material such as metal or plastic. In a preferred embodiment the suture retainer is constructed of a bio-compatible plastic. Additionally, the suture retainer may be constructed of multiple pieces, wherein the suture retainer and lever are assembled utilizing known methods of mechanical fastening or through the use of an adhesive. It is further contemplated that the suture retainer and lever may be integrally formed, such as through the use of injection molding.

Referring now to FIGS. 5-7 there is shown the distal end portion of the suture trimmer 10 in accordance with the present invention in use. As shown, a suture loop 150 has been formed utilizing a length of suture, wherein the suture loop includes a knot K and two free ends, S and S', of suture extending therefrom.

As illustrated in FIG. 5, the suture retainer 28 has been withdrawn into the bore of the shaft assembly 20 thereby allowing at least one free end of suture S to be disposed through the groove 54 formed in the fitting and groove 19 formed in the wall of the elongated member 25 and extend out the opening 23 formed in the side of the elongated member 25.

Referring now to FIG. 6, there is shown the distal tip of the suture trimmer in accordance with the present invention wherein the suture retainer 28 has been released. The biasing member is coupled to the proximal end of the suture retainer, causing the suture retainer to advance distally and be received within the bore of the distal end of the shaft assembly. As shown the suture protector 26 shields the suture S, S' from the edge of the opening 23 formed in the elongated member 25. The suture protector 26 ensures that the free end of the suture S cannot contact the edge of the opening 23 formed in the elongated member 25 which may be sharp. If the suture were allowed to contact the edge of the opening, a nick or cut may be formed in the suture, this may lead to failure of the suture before the knot can be advanced and tightened by applying a force to the free end of the suture. If the suture were to fail the surgeon would be required to place a second suture loop adjacent to the first suture loop and repeat the process of advancing and tightening the knot. Therefore, the suture protector 26 prevents the suture from being cut or abraded by the edge of the opening which may lead to failure of the suture.

Referring now to FIG. 7, there is shown a partial view of the distal tip of the suture trimmer 10 in accordance with the present invention wherein the cutting member 60 has been actuated to cut the sutures after the suture loop has been tightened as shown. Upon actuation, the cutting edge 63 advances from a shielded position within the distal tip portion of the shaft assembly 20. The cutting member 60 is advanced from the shielded position by applying a force to the lever 45, the lever 45 being coupled to the proximal end of the cutting member 10. As described above, the cutting member 60 is actuated by pulling back on the lever 45, thereby advancing the lever towards the proximal end of the suture trimmer 10 and compressing a second biasing member disposed within the handle. As shown the cutting member 60 includes a sharpened cutting edge 63. It is further contemplated that the proximal edge 23' of the opening 23 may also be sharpened to assist in cutting the suture. As described above and illustrated in FIG. 7, the cutting member 60 of the suture trimmer 10 moves relative to the elongated member 25 of the shaft assembly 20.

Referring now to FIG. 8 there is shown an alternative embodiment of a suture trimmer 100 in accordance with the present invention. As shown in FIG. 8, the suture trimmer 100 comprises a handle 130, an elongated shaft assembly 120, a distal tip fitting 150, a first lever 145 and a second lever 141. As shown in FIG. 8, the first lever 145 is configured to rotate R about the handle 130 in addition to being configured to be translated along an axis extending through the handle 130. The second lever 141 is configured to translate along an axis extending through the handle 130. The functionality of the first and second levers will be described in greater detail below with reference to FIG. 9. It is further contemplated that the first lever 145 may be embodied having a generally cylindrical shape and being disposed about the distal end of the handle. For example, the first lever 145 may be a ring.

Referring now to FIG. 9, there is shown the elongated shaft assembly 120 of the suture trimmer 100. As shown the elongated shaft assembly 120 comprises a hollow elongated member 125 having a proximal end 129 and a distal end 127. An opening 123 is formed in the wall of the elongated member 125 adjacent to the distal end 127 thereof. The opening 123 further configured to include a sharpened cutting edge. The sharpened cutting edge 118 being formed on the proximal end of the opening 123. The elongated member 125 may be constructed of a bio-compatible metal such as stainless steel, titanium or a bio-compatible coated material. Alternatively, the elongated member may be constructed of a bio-compatible plastic. The elongated member in a preferred embodiment has a circular cross-sectional profile, though it is contemplated that the elongated member may be constructed having other cross-sectional profiles such as square, triangular, or oval.

A suture retaining member 128 is disposed within the bore of the elongated member 125. The suture retaining member 128 includes an elongated member having a proximal end 137 and a distal end 131. A suture receiving groove 133 is formed in the distal end of the suture retaining member. The suture retaining member 128 is slidably and rotatably disposed within the bore of the elongated member 125. The suture retaining member 128 may be coaxially disposed within the bore of the elongated member 125, or arranged in an offset manner. The proximal end of the suture retaining member is coupled to the first and second levers of the suture trimming device, the function of which will be described in detail below.

The shaft assembly 120 may further include a fitting 150 may be disposed adjacent to the distal end 127 of the shaft assembly 120. The fitting 150 having a cross-sectional size no greater than that of the elongated member 125. The fitting 150 further including a groove 154 formed therein, wherein the groove 154 is configured to receive at least one length of suture therethrough. In a preferred embodiment, the groove 154 is configured to receive at least two sutures therethrough. The distal face of the fitting 150 is configured to engage a knot formed in a suture loop, thereby enabling the suture trimmer 100 to be utilized as a knot positioner and advance the knot to an incision site. The face of the fitting may be formed having a convex, concave, or flat surface. Alternatively, the face may be formed at an angle relative to an axis extending through the shaft assembly.

As shown in FIG. 9, the proximal end 129 of the shaft assembly 120 is connected to a handle 130. Handle 130 comprises a generally cylindrical casing 180 having an open interior chamber 135 and an axial slot 138 as shown in FIG. 8. A slider assembly 210 is reciprocatably disposed within the chamber 135, the slider assembly having a proximal end 281 and a distal end 282, the distal end 282 coupled to the proximal end 137 of the suture retainer 128. The slider assembly further including a first lever 145 and a second lever 141 coupled to the slider assembly 210 as shown in FIG. 8. A biasing member 290 is further disposed within the chamber 135 wherein the biasing member 290 is disposed in a space proximal the proximal end of the slider, the biasing member applying a force to the slider assembly so that the slider will remain in a distally advanced position. It is further contemplated that the suture trimmer 100 may include more than one biasing member. For example, two biasing members may be provided in combination and configured to provide a progressive spring rate.

The handle, slider, and levers may be manufactured of materials such as metals or plastics. In a preferred embodiment, the handle and levers are manufactured of plastic utilizing an injection molding process.

As shown in FIG. 9 the slider assembly 210 is constructed of a first member 280 having a proximal end 281, a distal end 282, a reduced diameter portion 284 and an enlarged diameter portion 286 disposed therebetween. The first member 280 further includes a plurality of members 285 disposed radially about a reduced diameter portion 284 of the first member 280. A rotating ring 200 is rotatably disposed about the reduced diameter portion 284. The rotating ring further includes and engaging member 205, wherein the engaging member is configured to engage one of the plurality of members 285 extending radially about the reduced diameter portion.

The proximal end 281 is further configured to receive a basing means 290. The biasing means may comprise a spring, elastic foam or devices that have similar mechanical properties.

The slider assembly and the suture retainer may be constructed as a unitary member or alternatively may be constructed of multiple pieces which are then assembled using known manufacturing methods.

Referring now to FIG. 8, the first lever 145 is coupled to the rotating ring 200, wherein a pin (not shown) is utilized to couple the first lever 145 to the rotating ring 200. By applying a rotational force 289 to the rotating ring causes the engaging member 205 to engage at least one of the plurality of members 285, thereby causing the suture retainer 280 to rotate within the shaft assembly 120. The second lever 141, shown in FIG. 8, is coupled to the increased diameter portion 285 of the slider assembly 210. The second lever 141 may be connected through the use of a pin (not shown) disposed within the increased diameter portion, the pin extending through a groove formed in the handle as shown in FIG. 8. A force may be applied to the second lever, thereby causing the suture retainer 128 and the second lever to be displaced proximally, the suture retainer 128 moving proximally within the elongated member 125 of the shaft assembly 120.

Referring now to FIGS. 10-13, there is shown a partial view of the distal tip of the suture trimmer 100 in accordance with the present invention disposed in various states of use, each of which will be described in detail below with reference to the figures.

Referring now to FIG. 10, there is shown the distal end of the suture trimmer 100, wherein the suture retaining member 128 is shown disposed in a distally advanced position. A suture loop has been formed in tissue as shown, the suture loop comprises a knot K formed in a loop of suture, wherein the two free ends S and S' of the suture extend from the knot.

Referring now to FIG. 11 there is shown the distal tip, wherein the suture retainer 128 has been retracted within the elongated member of the shaft assembly 120 by applying a force to the second lever 141. The two free ends of the suture as disposed through a groove 154 formed in the fitting 150 and distal end of the elongated member 125, the two free ends of suture extend through the opening 123 formed within the elongated member 125.

Referring now to FIG. 12, there is shown the distal tip of the suture trimmer 100 wherein the force applied to the second lever 141 has been released, thereby allowing the suture retaining member 128 to advance distally within the bore of the elongated member 125. As shown, in FIG. 12, the two free ends of the suture extend through the opening 133 formed in the distal end of the suture retaining member 128. Additionally, a rotational force has been applied to the first lever 145, causing the suture retaining member to rotate within the bore of the shaft assembly. By rotating the suture retaining member 128, the groove 154 is effectively closed, thus retaining the two free ends of the suture within the distal tip of the suture trimmer 100. Furthermore, by rotating the suture retaining member 128 as shown this aligns the two free ends of the suture with the sharpened cutting edge 163 formed in the proximal end 123' of the opening 123. Additionally, as shown, the distal end of the fitting has been utilized to advance the knot K onto the tissue, whereby the knot K can be tightened by pulling up on one of the free ends of the suture S/S'.

Referring now to FIG. 13, there is shown the suture loop after an axial force has been applied to the first lever 145 thereby retracting the suture retaining member 128 within the bore of the elongated member and advancing the two free ends of the suture into contact with the sharpened cutting edge 163 formed in the opening 123, whereby the sharpened cutting edge 163 severs the free ends of the suture adjacent to the knot K as shown.

As described above with reference to FIGS. 8-13, it shall be understood that the cutting member of the suture trimmer 100 remains stationary in use. As shown in FIGS. 10-13, a piece of suture to be severed is brought to the cutting edge. The suture us severed due to the interference between the suture, the opening 133 formed in the suture retaining member 128 and the cutting edge 118.

Referring now to FIGS. 14-18 there is shown an alternative suture trimmer 300 in accordance with the present invention. As shown in FIG. 14, the suture trimmer 300 comprises a handle portion 330, a shaft assembly 320 and a fitting 350 disposed on the distal end of the shaft assembly. The handle 330, shaft assembly 320 and fitting 350, of the suture trimmer 300 is similar to each of those described above. With regard to FIGS. 15-18, there is shown the suture trimmer 300 in accordance with FIG. 14 in use.

Referring now to FIG. 15 there is shown yet another alternative embodiment of a suture trimmer in accordance with the present invention. As shown in FIG. 15, the suture trimmer 300 includes a shaft assembly, a fitting disposed on the distal tip of the shaft assembly and a lever. The suture trimmer 300 includes a retractable, indicated by reference number 400, elongated member 325 connected to a lever 345, the lever connected to a handle. In addition to being retractable, the elongated member 325 is further configured to rotate, indicated by the reference number 410, about an axis extending between the distal end and proximal end of the suture trimmer 300.

Referring now to FIG. 15, there is shown the distal tip of the suture trimmer 300 wherein the elongated member 325 of the shaft assembly 320 has been retracted, thereby exposing the groove 354 through which the free end(s) of the suture may be disposed as shown.

Referring now to FIG. 16, there is shown the distal tip, wherein the force applied to retract the elongated member 325 has been released, thereby allowing the elongated member 325 to advance as shown. The elongated member 325 is utilized to close the groove 354 when advanced in a distal position as shown in FIG. 16, thereby retaining the free ends of the sutures within the groove 354 as shown. Furthermore, after allowing the elongated member to advance as shown, the distal tip of the suture trimmer may be utilized to advance the knot K and substantially close the suture loop. Referring now to FIG. 17, there is shown the distal tip of the suture trimmer 300, wherein the elongated member 325 has been rotated counter-clockwise relative to the suture retainer 328. By rotating the elongated member 325 as shown, draws the free ends of the suture to a cutting edge 363 formed in the elongated member 325.

Referring now to FIG. 18, there is shown the suture trimmer 300 in accordance with the present invention. As shown in FIG. 18, the elongated member 325 has been retracted relative to the suture retaining member 328. By retracting the elongated member 325, the free ends of the suture are brought into contact with the cutting edge 363 formed within the elongated member 325, thus trimming the free ends of the suture close to the knot K as shown.

Although the suture trimmer 300 is described wherein the elongated body is rotated relative to the suture retaining member 128, it is contemplated that the elongated member may be held stationary and the suture retaining member may be rotated therein. Still further it is contemplated that both the elongated member and the suture retaining member may be rotated respectively.

Still further, it shall be understood that although the embodiments illustrated herein have been described as utilizing levers to advance/actuate/move various features disposed within or upon the suture trimmers it shall be understood that other mechanical devices and assemblies may be utilized to perform the same tasks without departing from the scope of the present invention.

Although the present invention has been described in considerable detail with reference to certain preferred embodiments, it is contemplated that one skilled in the art may make modifications to the device herein without departing from the scope of the invention. Therefore, the scope of the appended claims should not be considered limited to the embodiments described herein.

The invention claimed is:

1. A suture trimmer, the suture trimmer comprising:
a shaft having a proximal end and a distal end and an axis therebetween, the shaft having a groove formed in the side thereof, the groove in communication with an opening formed in the side of the shaft, the opening disposed proximal the distal end;
a fitting disposed within a bore of the distal end of the shaft, the fitting having a cross-sectional size no greater than a cross-sectional size of the distal end of the shaft, a tapered distal end portion, and a groove in communication with the groove formed in the side of the shaft;
a cutting member slidably disposed within the shaft; and
a suture retainer slidably disposed within the shaft.

2. The suture trimmer according to claim 1, wherein suture trimmer further includes a handle, the handle disposed adjacent the proximal end of the shaft.

3. The suture trimmer according to claim 2, wherein the handle further includes a first lever and a second lever, the first lever operatively coupled to the suture retainer and the second lever operatively coupled to the cutting member.

4. The suture trimmer according to claim 3, wherein the main handle further includes at least one biasing member, the biasing member connected to at least one of the cutting member and suture retainer.

5. The suture trimmer according to claim 4, wherein the cutting member includes a sharpened portion, the sharpened portion adapted to engage a fitting to sever suture when suture is disposed through the groove and opening.

6. The suture trimmer according to claim 5, wherein the sharpened edge of the cutting member is retracted within the shaft until withdrawn by applying a force to the second lever.

7. The suture trimmer according to claim 6, wherein the suture is disposed within the groove and opening by retracting a suture guide within the shaft by applying a force to the first lever.

8. A method for trimming suture, the method comprising:
disposing a suture loop within tissue of a patient, the suture loop including at least one knot and at least one free end of suture;
disposing the free end of suture through a groove and an opening formed in a distal end of a suture trimmer, wherein the suture trimmer comprises a fitting disposed within a bore of the distal end of the suture trimmer, the fitting having a cross-sectional size no greater than a cross-sectional size of the distal end of the suture trimmer, a tapered distal end portion, and a groove in communication with the groove formed in the side of the suture trimmer;
and
actuating a cutting member within the suture trimmer, the cutting member configured to sever the suture disposed in the opening.

9. The method according to claim 8, further including positioning the knot with the distal tip of the suture trimmer.

10. The method according to claim 8, wherein disposing the free end of the suture through a groove and opening comprises retracting a suture retainer within the suture trimmer.

11. The method according to claim 10, wherein activating a cutting member comprises applying a force to a lever in communication with the cutting member, the cutting member being retracted from a shielded position within a shaft of the suture trimmer to an exposed position, the exposed position configured to trim the suture.

12. A suture trimmer, the suture trimmer comprising:
a shaft having a proximal end and a distal end defining an axis therebetween, the shaft including a groove formed in the side thereof, the groove in communication with an opening formed in the side of the shaft, the opening disposed proximal the distal end;
a fitting disposed within a bore of the distal end of the shaft, the fitting having a cross-sectional size no greater than a cross-sectional size of the distal end of the shaft, a tapered distal end portion, and a groove in communication with the groove formed in the side of the shaft;
a cutting member formed within an edge of the opening; and
a suture retainer having a proximal end and a distal end, the suture retainer disposed within a bore of the shaft.

13. The suture trimmer according to claim 12, wherein the suture trimmer further includes a handle, the handle connected to the proximal end of the suture retainer.

14. The suture trimmer according to claim 13, wherein the suture trimmer further includes at least one biasing member disposed within a chamber of the handle, the biasing member operatively connected to the shaft.

15. The suture trimmer according to claim 14, wherein the suture trimmer further includes at least one lever, the lever operatively connected to the shaft.

16. The suture trimmer according to claim 15, wherein the shaft may be moved relative to the suture retainer wherein the cutting edge of the shaft is configured to sever suture when suture is disposed through the groove and opening.

17. The suture retainer according to claim 12, wherein the suture retainer includes a handle, the handle including at least one lever, the lever operatively connected to the suture retainer.

18. The suture retainer according to claim 17, wherein the handle is rotatable relative to the axis of the shaft and configured to rotate the suture retainer relative to the shaft assembly.

19. The suture retainer according to claim 18, wherein the suture retainer includes a second lever, the second lever operatively coupled to the suture retainer, the second lever and suture retainer further configured to move along the axis of the shaft when a force is applied thereto.

20. The suture retainer according to claim 19, wherein the suture retainer further includes at least one biasing member disposed within a chamber of the handle, the biasing member operatively connected to the suture retainer.

* * * * *